United States Patent
Liao et al.

(10) Patent No.: US 8,590,394 B2
(45) Date of Patent: Nov. 26, 2013

(54) LOCAL ANTISTRESS TEST PLATFORM AND TEST APPARATUS

(75) Inventors: Zuomin Liao, Shenzhen (CN); Minghung Shih, Shenzhen (CN)

(73) Assignee: Shenzhen China Star Optoelectronics Technology Co., Ltd., Shenzhen (CN)

( * ) Notice: Subject to any disclaimer, the term of this patent is extended or adjusted under 35 U.S.C. 154(b) by 105 days.

(21) Appl. No.: 13/264,874

(22) PCT Filed: Jul. 20, 2011

(86) PCT No.: PCT/CN2011/077401
§ 371 (c)(1),
(2), (4) Date: Oct. 17, 2011

(87) PCT Pub. No.: WO2012/167485
PCT Pub. Date: Dec. 13, 2012

(65) Prior Publication Data
US 2013/0019691 A1    Jan. 24, 2013

(30) Foreign Application Priority Data
Jun. 8, 2011   (CN) .......................... 2011 1 0151930

(51) Int. Cl.
*G01N 3/02* (2006.01)
*G01N 3/00* (2006.01)

(52) U.S. Cl.
USPC ............................................ 73/856; 73/794

(58) Field of Classification Search
USPC ......................................... 73/749, 856, 794
See application file for complete search history.

(56) References Cited

U.S. PATENT DOCUMENTS

| | | | |
|---|---|---|---|
| 5,801,545 A * | 9/1998 | Takekoshi et al. | 324/750.25 |
| 6,353,466 B1 * | 3/2002 | Park | 349/58 |
| 6,486,927 B1 * | 11/2002 | Kim | 349/1 |
| 6,536,258 B1 | 3/2003 | Mostaghel | |
| 7,679,393 B2 * | 3/2010 | Kuo | 324/760.01 |
| 7,777,828 B2 * | 8/2010 | Shim et al. | 349/58 |
| 7,942,393 B2 * | 5/2011 | Zhu et al. | 269/75 |
| 2006/0137465 A1 * | 6/2006 | Lee et al. | 73/794 |

FOREIGN PATENT DOCUMENTS

| | | |
|---|---|---|
| CN | 2077994 | 5/1991 |
| CN | 1395087 | 2/2003 |
| CN | 2935129 | 8/2007 |
| CN | 201096689 | 8/2008 |
| CN | 101837848 | 9/2010 |
| TW | 498161 | 8/2002 |

* cited by examiner

*Primary Examiner* — Lisa Caputo
*Assistant Examiner* — Jonathan Dunlap
(74) *Attorney, Agent, or Firm* — Muncy, Geissler, Olds & Lowe, PLLC

(57) ABSTRACT

Disclosed is a local antistress test platform, comprising a test frame and a weight test rod for providing a local stress to a tested panel by adding weights. The local antistress test platform further comprises a movable test hole table for fixing the weight test rod; the movable test hole table is removably jointed to the test frame. The present invention also relates to local antistress test apparatus. The local antistress test platform and the test apparatus can easily locate the antistress test position and be adaptable to panel test for panels of different sizes.

13 Claims, 4 Drawing Sheets

LOCAL ANTISTRESS TEST PLATFORM AND TEST APPARATUS

CROSS-REFERENCE TO RELATED APPLICATIONS

This application is the National Stage of International Application No. PCT/CN2011/077401 filed Jul. 20, 2011, which claims the benefit of Chinese Application No. 201110151930.3, filed Jun. 8, 2011, the disclosures of which are incorporated herein by reference in their entireties.

BACKGROUND OF THE INVENTION

1. Field of the Invention

The present invention generally relates to the field of panel test, and more particularly to a local antistress test platform and a test apparatus having a movable test hole.

2. Description of Prior Art

As the big screen TV gets popular, the requirements of the screen panel, and particularly the big screen panel become larger and larger in the market. For guaranteeing the quality of the panel, a local antistress test needs to be proceeded to the panel before leaving the factory. The local antistress test is to apply a certain local stress to the panel to press the panel locally. The recovery ability of the panel after stress release can be confirmed by checking whether a spot exists at the test position with powering up the panel. The local antistress test platform according to prior art is a platform having a fixing hole as shown in FIG. 1. As such test platform with fixing hole is utilized, the test platform or the tested panel needs to be relocated again and again because the hole is at a fixed position. The drawbacks of test inconvenience and location inaccuracy are obvious in such test platform. As shown in FIG. 2, for testing the marked five points on the tested panel, the test platform needs to be relocated again and again to align the center of the central hole with the test position of the tested panel. It is more difficult for the test platform to locate the test position of the tested panel. Besides, as shown in FIG. 2, the length of the tested panel is a and the width is b. The length of the test platform needs to as larger as that of the test platform shown in figure for possible antistress test of the five test positions. The required lengths of the test platform for the panels having different sizes, different L/W ratios are also different accordingly. Due to the inadaptability of such test platform, kinds of test platforms for the panels having different sizes are necessary to be prepared. In case that unisize test platform is utilized, Drawbacks of location inconvenience and large occupied space exist when test is proceeded to a panel with small size.

Consequently, there is a need to provide a local antistress test platform and test apparatus to solve the existing problems of prior arts.

SUMMARY OF THE INVENTION

For solving the aforesaid problems of difficulty of locating the test position precisely and inadaptability to panel test for panels of different sizes in prior arts, the present invention provides a local antistress test platform and a test apparatus which is capable of easily locating the antistress test position and adaptable to panel test for panels of different sizes.

An objective of the present invention is to provide a local antistress test platform and the local antistress test platform comprises a test frame, fixing the local antistress test platform; and a weight test rod, providing a local stress to a tested panel by adding weights, wherein the local antistress test platform further comprises:

a movable test hole table, fixing the weight test rod;
the movable test hole table is removably jointed to the test frame;
a rolling guide, positioned on the test frame;
the movable test hole table comprises a joint slot slidably jointed to the rolling guide and a fixing element for fixing the movable test hole table on the rolling guide;
the fixing element comprises a fixing hole formed at the movable test hole table and a fixing nut for fixing the movable test hole table on the rolling guide via the fixing hole;
the movable test hole table further comprises a sliding pulley for reducing a frictional force between the test hole table and the rolling guide;
the test frame further comprises a dividing rule attached to at least one side of the rolling guide to measure an antistress test position on the tested panel;
the dividing rule comprises an indicator to point the antistress test position of the weight test rod on the tested panel.

Another objective of the present invention is to provide a local antistress test platform comprising:

a test frame, fixing the local antistress test platform; and
a weight test rod, providing a local stress to a tested panel by adding weights,
wherein the local antistress test platform further comprises:
a movable test hole table, fixing the weight test rod;
the movable test hole table is removably jointed to the test frame.

Another objective of the present invention is to provide a local antistress test apparatus, comprising: a local antistress test platform for proceeding a local antistress test to a panel, comprising:

a test frame, fixing the local antistress test platform; and
a weight test rod, providing a local stress to a tested panel by adding weights,
wherein the local antistress test platform further comprises:
a movable test hole table, fixing the weight test rod;
the movable test hole table is removably jointed to the test frame.

In one embodiment of the present invention, the local antistress test platform further comprises a rolling guide positioned on the test frame; the movable test hole table comprises a joint slot slidably jointed to the rolling guide.

In one embodiment of the present invention, the movable test hole table further comprises a fixing element for fixing the movable test hole table on the rolling guide.

In one embodiment of the present invention, the fixing element comprises a fixing hole formed at the movable test hole table and a fixing nut for fixing the movable test hole table on the rolling guide via the fixing hole.

In one embodiment of the present invention, the movable test hole table further comprises a sliding pulley for reducing a frictional force between the test hole table and the rolling guide.

In one embodiment of the present invention, the test frame further comprises a dividing rule attached to at least one side of the rolling guide to measure an antistress test position on the tested panel.

In one embodiment of the present invention, the dividing rule comprises an indicator to point the antistress test position of the weight test rod on the tested panel.

Comparing with the local antistress test platform of prior arts having problems of difficulty of locating the test position precisely and inadaptability to panel test for panels of different sizes, the local antistress test platform and the test apparatus of the present invention have a movable test hole is capable of easily locating the antistress test position and adaptable to panel test for panels of different sizes accordingly.

For a better understanding of the aforementioned content of the present invention, preferable embodiments are illustrated in accordance with the attached figures for further explanation:

DETAILED DESCRIPTION OF THE INVENTION

The following descriptions for the respective embodiments are specific embodiments capable of being implemented for illustrations of the present invention with referring to appended figures. For example, the terms of up, down, front, rear, left, right, interior, exterior, side, etcetera are merely directions of referring to appended figures. Therefore, the wordings of directions are employed for explaining and understanding the present invention but not limitations thereto.

In figures, the elements with similar structures are indicated by the same number.

Figure 3:
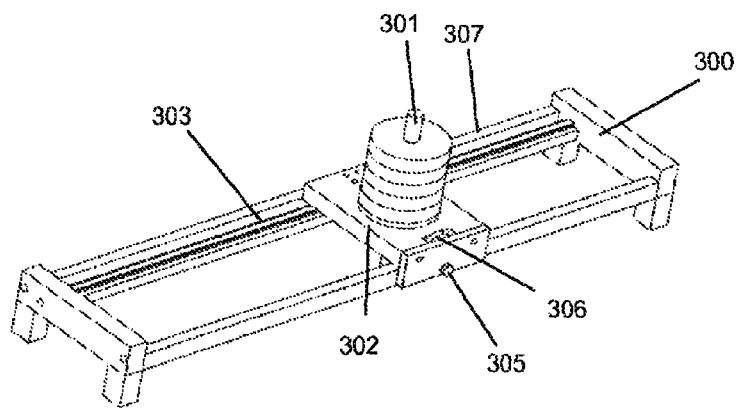
FIG. 3 shows a structure diagram of a local antistress test platform according to a preferable embodiment of the present invention.
Figure 4:
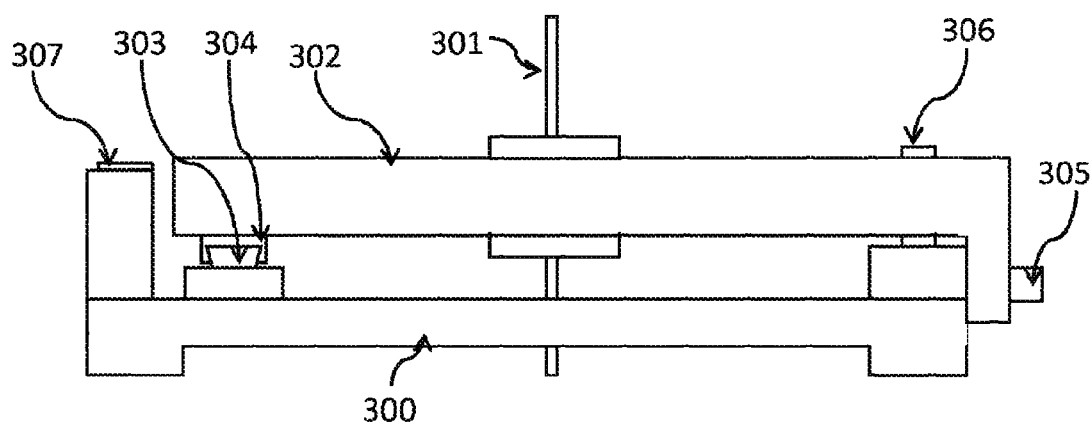
FIG. 4 shows a sectional diagram of a local antistress test platform according to the first preferable embodiment of the present invention.

In diagrams of a local antistress test platform according to the preferable embodiment of the present invention shown in FIG. 3 and FIG. 4, the local antistress test platform comprises a test frame 300, a weight test rod 301 positioned on the test frame 300 and a movable test hole table 302. The test frame 300 is employed to fix the local antistress test platform. The weight test rod 301 is employed to provide a local stress to a tested panel by adding weights. The movable test hole table 302 is employed to fix the weight test rod 301 and removably jointed to the test frame 300.

With having a movable test hole equipped in the present invention, an adjustable test of the local antistress test platform can be achieved. During use, the test frame 300 is located above the tested panel. The movable test hole table 302 can be located above the antistress test position of the tested panel without the test frame 300 to achieve the precise location for the antistress test position of the tested panel because the movable test hole table 302 and the test frame 300 are removably jointed with each other. Then, the weight test rod 301 is employed for adding weights or other heavy stuff to proceed the local antistress test at the test position of the tested panel. The local antistress test platform of the present invention can easily locate the antistress test position due to the adjustability thereof and be adaptable to the panel test for panels of different sizes.

In diagrams of a local antistress test platform according to the preferable embodiment of the present invention shown in FIG. 3 and FIG. 4, the local antistress test platform further comprises a rolling guide 303 positioned on the test frame 300. The movable test hole table 302 comprises a joint slot 304. The joint slot 304 is slidably jointed to the rolling guide 303.

Figure 5:
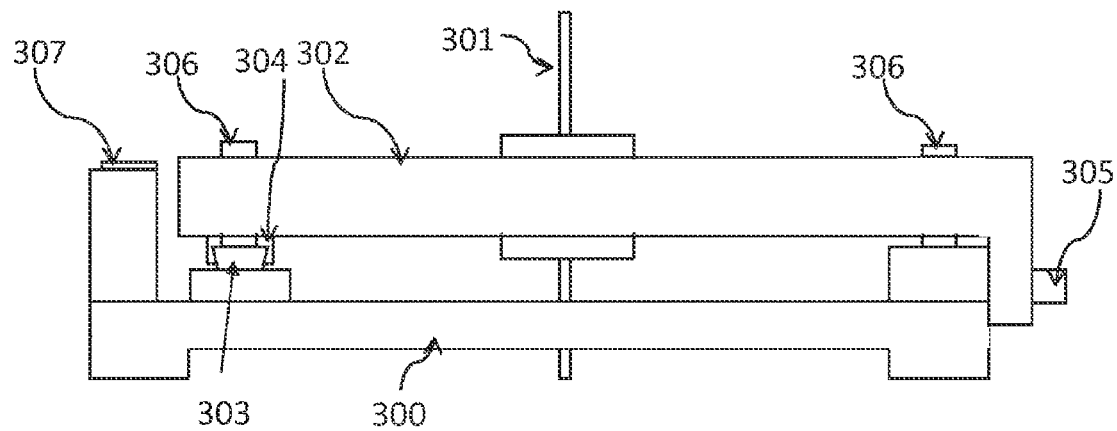
FIG. 5 shows a sectional diagram of a local antistress test platform according to the second preferable embodiment of the present invention.
Figure 6:
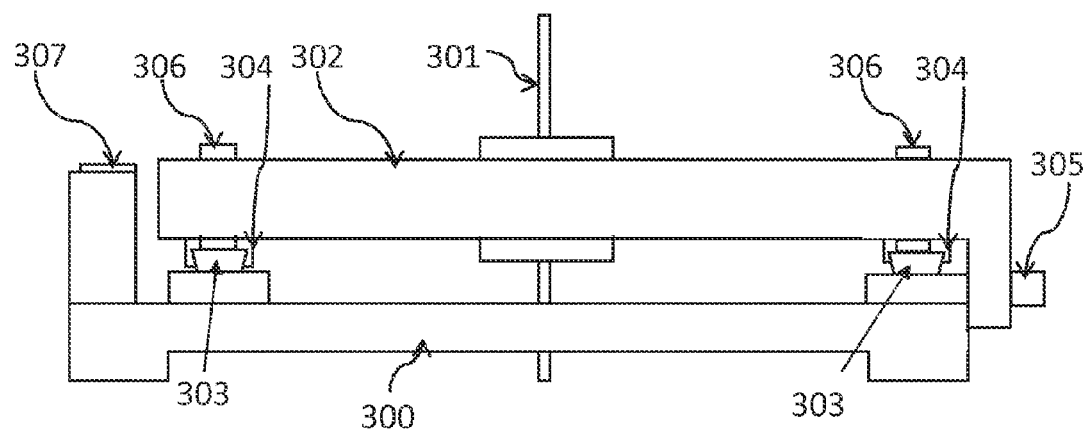
FIG. 6 shows a sectional diagram of a local antistress test platform according to the third preferable embodiment of the present invention.

As shown in FIG. 3, the movable test hole table 302 is slidably jointed to the rolling guide 303 through the joint slot 304. Such slidable joint leads to a great guiding function of the rolling guide 303 for the movable test hole table 302. As long as positioning the rolling guide 303 and the test positions of the tested panel in parallel, the antistress test for several test positions in a straight line can be proceeded without moving the test frame 300. Therefore, locating the antistress test positions and obtaining precise measurements is easier and test time can be shortened. The rolling guide 303 and the joint slot 304 can be positioned at one side of the test frame 300 according to user's demands (as shown in FIG. 4 and FIG. 5). Alternatively, the rolling guide 303 and the joint slot 304 can be positioned at two sides of the test frame 300 (as shown in FIG. 6)

In diagrams of a local antistress test platform according to the preferable embodiment of the present invention shown in FIG. 3 and FIG. 4, the movable test hole table 302 further comprises a fixing element. The fixing element is employed to fix the movable test hole table 302 on the rolling guide 303; the fixing element comprises a fixing hole formed at the movable test hole table 302 and a fixing nut 305. The fixing nut 305 is employed to fix the movable test hole table on the rolling guide 303 via the fixing hole.

With the fixing element, the antistress test platform of the present invention not only has good adaptability and easy operationality, and also promotes the test reliability and repeatability of the test results. During the antistress test, the test frame 300 can be located above the tested panel and the movable test hole table 302 can be fixed on the rolling guide 303. In this embodiment, the combination of the fixing hole and the fixing nut 305 is utilized to achieve the aforesaid fixture. Then, required weights are added to the weight test rod 301 to proceed the local antistress test at the test position of the tested panel. Accordingly, it can be ensured that the movable test hole table 302 is not moved during the antistress test to promote the reliability of the antistress test.

In diagrams of a local antistress test platform according to the preferable embodiment of the present invention shown in FIG. 3 and FIG. 4, the movable test hole table 302 further comprises a sliding pulley 306. The sliding pulley 306 is employed to reduce a frictional force between the test hole table 302 and the rolling guide 303.

The sliding pulley 306 is utilized for jointing the movable test hole table 302 and the rolling guide 303, together. Meanwhile, the sliding pulley 306 is also utilized for jointing the movable test hole table 302 and the test frame 300. The sliding pulley 306 can be positioned at the side of the test frame 300 without the rolling guide 303 (as shown in FIG. 4). Alternatively, the sliding pulley 306 can be positioned at both sides of the test frame 300 (as shown in FIG. 5 and FIG. 6). The sliding pulley 306 is more beneficial to the precise location of the antistress test position. A plurality of sliding pulleys 306 can be positioned at each side of the test frame 300. The amount of the sliding pulleys 306 can be decided according to the user's demands and cost of the product overall.

In diagrams of a local antistress test platform according to the preferable embodiment of the present invention shown in FIG. 3 and FIG. 4, the test frame 300 further comprises a dividing rule 307 attached to at least one side of the rolling guide 303 to measure an antistress test position on the tested panel. The dividing rule 307 comprises an indicator to point the antistress test position of the weight test rod 301 on the tested panel.

By utilizing the local antistress test platform of the present invention, the antistress test for several test positions can be proceeded with merely one location of the test frame 300. Therefore, the dividing rule 307 of the test frame 300 is capable of locating the several test positions more precisely. If two dividing rules 307 are attached to the two sides of the test frame 300, it is preferable to attach the two dividing rules 307 relatively (the scale of one dividing rule 307 gradually increases and the scale of the other dividing rule 307 gradually decreases from one end of the test frame 300 to the other end). Accordingly, the precise location of the antistress test position can be derived as the antistress tests are proceeded along either direction of the test frame 300.

The weight test rod 301 is positioned on the movable test hole table 302. The antistress test position hides in the movable test hole table 302 where the operator cannot see. The location of the antistress test position of the tested panel is inconvenient. The indicator positioned on the dividing rule 307 for pointing the antistress test position of the weight test rod 301 on the tested panel eliminates the aforesaid inconvenience. Once the movable test hole table 302 is located to the position corresponding to the indicator of the dividing rule 307, and then the weight test rod 301 is located at the antistress test position on the tested panel which the operator demands and achieve the precise location for the antistress test position.

The present invention also relates to a local antistress test apparatus. The local antistress test apparatus utilizes the aforesaid local antistress test platform for proceeding a local antistress test to a panel. The benefits and the embodiments can be referred to the aforementioned preferable embodiments of the local antistress test platform.

Figure 7:
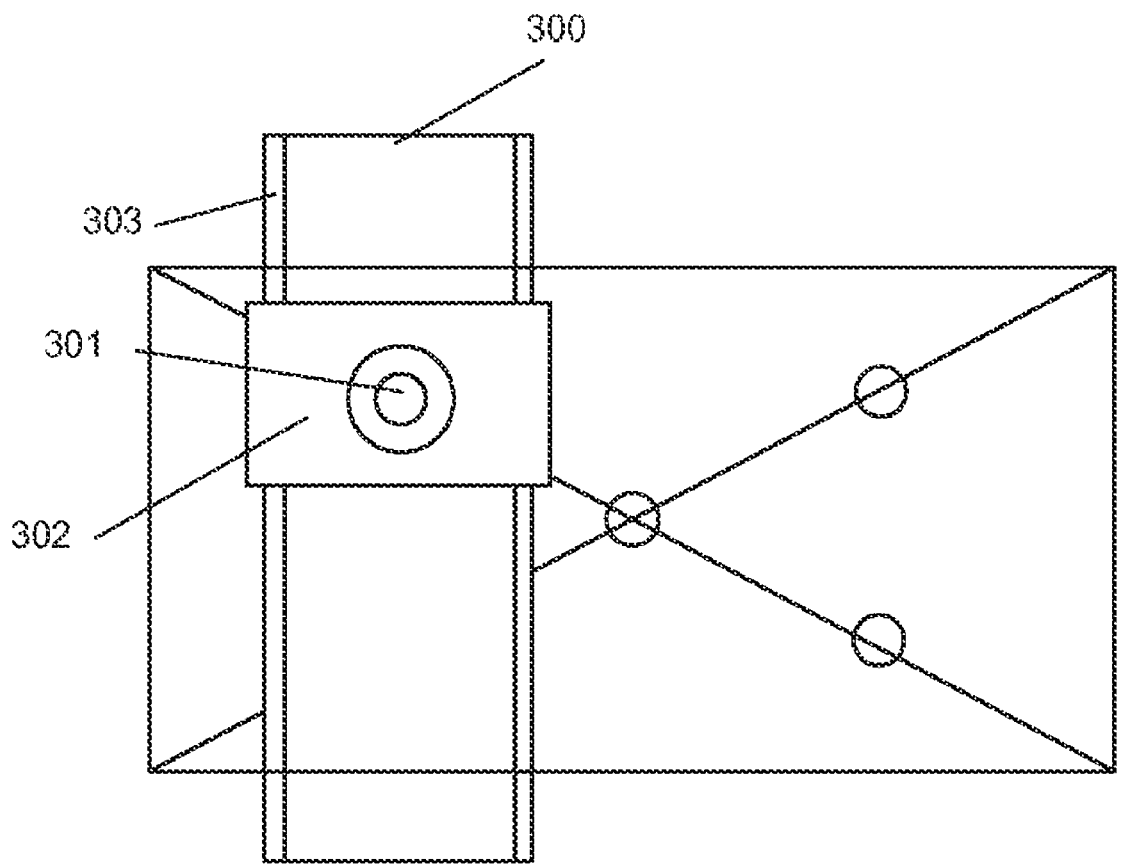
FIG. 7 shows an application diagram of the local antistress test platform according to preferable embodiments of the present invention.

The workflow is introduced hereafter with the diagrams of the local antistress test platform according to the preferable embodiment of the present invention shown in FIG. 3 and FIG. 7.

Preparation:

As shown in FIG. 7, the tested panel is cleaned with alcohol, before locating the antistress test position; the four corners of the panel area are checked for drawing the diagonal lines. Each of the diagonal lines is quartered and one to five points in figure can be marked. Lines and marks can be sketched on the clean paper in advance. Then, the sketched clean paper is placed under the panel. Circles with 5 mm diameter are drawn on the panel with mark pen and compass. The points should be ensured at the center of the circles.

Test:

The tested panel is placed on a tabletop which is level, steady and not deformable.

The test frame 300 of the local antistress test platform is now located above the tested panel. The weight test rod 301 is moved along the rolling guide 303 and located at the antistress test position by utilizing the movable test hole table 302. (The location can be achieved by utilizing the indicator of the dividing rule 307). The fixing nut 305 is screwed tie to fix the movable test hole table 302.

The required weights are added to the weight test rod 301 to proceed the local antistress test at the panel test position through the hole of the movable test hole table 302. The stress remains for one minute before the weights are removed. Then, the judgment of the local antistress ability is executed with powering up the panel after five minutes.

The aforesaid test steps are repeated for different test position and the local antistress tests with different weights.

The verticality of the weight test rod 301 is extremely demanded during the antistress test. Friction between the weight test rod 301 and the weights needs to be avoided as possible to prevent the unbalance and inaccuracy of the stress.

Figure 1:
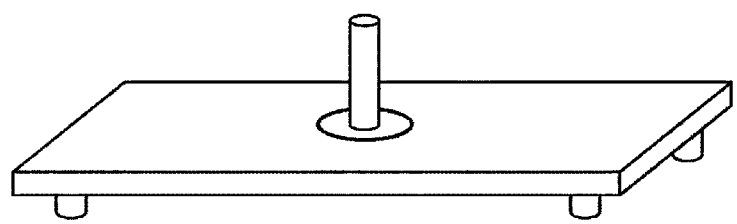
FIG. 1 shows a structure diagram of a local antistress test platform according to prior art.
Figure 2:
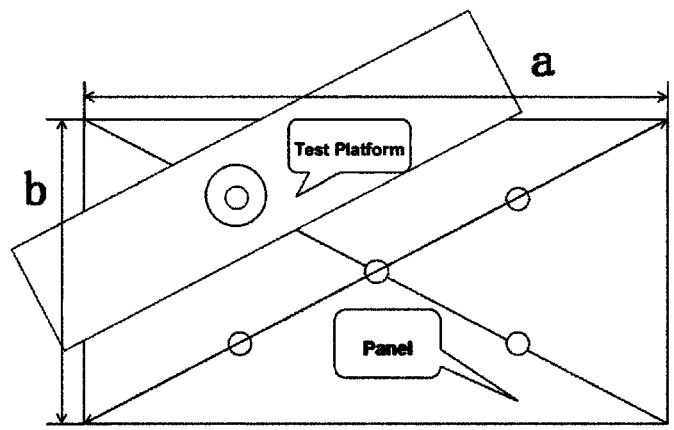
FIG. 2 shows an application diagram local antistress test platform according to prior art.

As the panel test is proceeded with the local antistress test platform of the present invention, the test platform only needs to be moved three times for the five point local antistress tests of the whole tested panel. Furthermore, the test platform with fixing holes according to prior occupies a large space. On the contrary, the extent of the local antistress test platform according to the present invention only needs to be slightly longer than the short side of the panel. As proceeding the test for the large panel, such as for the 16:9 main stream panel, the length L of the test platform is required to be larger than the panel width b as proceeding the test at the test position shown in FIG. 2. However, the length of the test platform according to the present invention can be equal to the width b. Consequently, with the same length of the test platform according to prior art, the test platform according to the present invention is capable of proceeding antistress test to a larger panel and adaptable to panel test for panels of different sizes.

As is understood by a person skilled in the art, the foregoing preferred embodiments of the present invention are illustrative rather than limiting of the present invention. It is intended that they cover various modifications and similar arrangements be included within the spirit and scope of the appended claims, the scope of which should be accorded the broadest interpretation so as to encompass all such modifications and similar structure.

What is claimed is:

1. A local antistress test platform, comprising:
a test frame, fixing the local antistress test platform; and
a weight test rod, providing a local stress to a tested panel by adding weights,
which is characterized in that the local antistress test platform further comprises:
a movable test hole table, fixing the weight test rod;
the movable test hole table is removably jointed to the test frame;
a rolling guide, positioned on the test frame;
the movable test hole table comprises a joint slot slidably jointed to the rolling guide and a fixing element for fixing the movable test hole table on the rolling guide;
the fixing element comprises a fixing hole formed at the movable test hole table and a fixing nut for fixing the movable test hole table on the rolling guide via the fixing hole;
the movable test hole table further comprises a sliding pulley for reducing a frictional force between the test hole table and the rolling guide;
the test frame further comprises a dividing rule attached to at least one side of the rolling guide to measure an antistress test position on the tested panel;
the dividing rule comprises an indicator to point the antistress test position of the weight test rod on the tested panel.

2. A local antistress test platform, comprising:
a test frame, fixing the local antistress test platform; and
a weight test rod, providing a local stress to a tested panel by adding weights,
which is characterized in that the local antistress test platform further comprises:
a movable test hole table, fixing the weight test rod;
the movable test hole table is removably jointed to the test frame,
wherein the local antistress test platform further comprises a rolling guide positioned on the test frame and the movable test hole table comprises a joint slot slidably jointed to the rolling guide.

3. The local antistress test platform of claim 2, characterized in that the movable test hole table further comprises a fixing element for fixing the movable test hole table on the rolling guide.

4. The local antistress test platform of claim 3, characterized in that the fixing element comprises a fixing hole formed at the movable test hole table and a fixing nut for fixing the movable test hole table on the rolling guide via the fixing hole.

5. The local antistress test platform of claim 2, characterized in that the movable test hole table further comprises a sliding pulley for reducing a frictional force between the test hole table and the rolling guide.

6. The local antistress test platform of claim 5, characterized in that the test frame further comprises a dividing rule attached to at least one side of the rolling guide to measure an antistress test position on the tested panel.

7. The local antistress test platform of claim 6, characterized in that the dividing rule comprises an indicator to point the antistress test position of the weight test rod on the tested panel.

8. The local antistress test platform of claim 2, characterized in that the test frame further comprises a dividing rule attached to at least one side of the rolling guide to measure an antistress test position on the tested panel.

9. The local antistress test platform of claim 8, characterized in that the dividing rule comprises an indicator to point the antistress test position of the weight test rod on the tested panel.

10. A local antistress test apparatus, comprising:
a local antistress test platform for proceeding a local antistress test to a panel, comprising:
a test frame, fixing the local antistress test platform; and
a weight test rod, providing a local stress to a tested panel by adding weights,
which is characterized in that the local antistress test platform further comprises:
a movable test hole table, fixing the weight test rod;
the movable test hole table is removably jointed to the test frame,
wherein the local antistress test platform further comprises a rolling guide positioned on the test frame and the movable test hole table comprises a joint slot slidably jointed to the rolling guide.

11. The local antistress test platform of claim 10, characterized in that the movable test hole table further comprises a fixing element for fixing the movable test hole table on the rolling guide.

12. The local antistress test apparatus of claim 11, characterized in that the fixing element comprises a fixing hole formed at the movable test hole table and a fixing nut for fixing the movable test hole table on the rolling guide via the fixing hole.

13. The local antistress test platform of claim 10, characterized in that the movable test hole table further comprises a sliding pulley for reducing a frictional force between the test hole table and the rolling guide;
the test frame further comprises a dividing rule attached to at least one side of the rolling guide to measure an antistress test position on the tested panel.

* * * * *